(12) United States Patent
Wang et al.

(10) Patent No.: US 6,703,382 B2
(45) Date of Patent: Mar. 9, 2004

(54) SMALL MOLECULE INHIBITORS TARGETED AT BCL-2

(75) Inventors: Shaomeng Wang, Saline, MI (US); Dajun Yang, Rockville, MD (US); Istvan J. Enyedy, Hamden, CT (US)

(73) Assignee: Georgetown University Medical Center, Washington, DC (US)

( * ) Notice: Subject to any disclaimer, the term of this patent is extended or adjusted under 35 U.S.C. 154(b) by 0 days.

(21) Appl. No.: 09/930,237

(22) Filed: Aug. 16, 2001

(65) Prior Publication Data

US 2002/0137732 A1 Sep. 26, 2002

Related U.S. Application Data

(60) Provisional application No. 60/225,661, filed on Aug. 16, 2000.

(51) Int. Cl.[7] ............... A61K 31/655; A61K 33/24; A61K 31/70; A61K 31/675; A61P 35/00
(52) U.S. Cl. ........................ 514/183; 540/482
(58) Field of Search ................ 540/482; 514/183

(56) References Cited

U.S. PATENT DOCUMENTS 3,170,929 A * 2/1965 Lowrie ................ 540/471

FOREIGN PATENT DOCUMENTS

| WO | WO 96/29403 A | 9/1996 |
|---|---|---|
| WO | WO 00/04901 A | 2/2000 |

OTHER PUBLICATIONS

Charles Gansser, "Derivatives of 5 6 11 12 Tetra Hydro Di Benzo–C G 1 2– Diazocine," *European Journal of Medicinal Chemistry*, vol. 10, No. 3, pp. 273–275 (1975).

Jia–Lun Wang, et al., "Structure–Based Discovery of an Organic Compound that Binds Bcl–2 Protein and Induces Apoptosis of Tumor Cells," *Proceedings of the National Academy of Sciences of the Unites States*, vol. 97, No. 13, pp. 7124–7129, (Jun. 30, 2000).

D. L. Kirkpatrick, et al., "Nitrobenzyl Derivatives as Bioreductive Alkylating Agents: Evidence for the Reductive Formation of a Reactive Intermediate," *J. Med. Chem.*, vol. 29, pp. 2048–2052, (1986).

Mark A. Smith, et al., "Cyclic Azo Dioxides. Synthesis and Properties of Bis(o–nitrosobenzyl) Derivatives," *J. Org. Chem.*, vol. 45, No. 23, pp. 4597–4602, (1980).

Istvan J. Enyedy, et al., "Discovery of Small–Molecule Inhibitors of Bcl–2 through Structure–Based Computer Screening," *J. Med. Chem.*, vol. 44, pp. 4313–4324, (Jan. 11, 2001).

* cited by examiner

*Primary Examiner*—Mark L. Berch
*Assistant Examiner*—Hong Liu
(74) *Attorney, Agent, or Firm*—Medlen & Carroll, LLP

(57) ABSTRACT

A method for promotion of cell death in tumor cells using tricylo-dibenzo-diazocine-dioxides that bind to a pocket of Bcl-2 and block the Bcl-2 anti-apoptotic function. A method of use of a compound of the general structural Formula (I) for use in treatment of cancer:

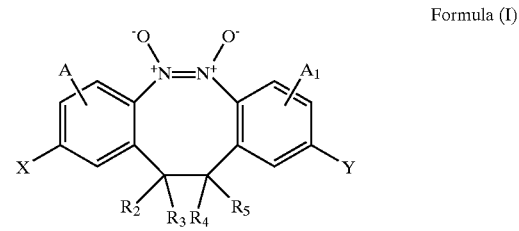

Formula (I)

wherein X and Y, and R and $R_1$, and $R_2$, $R_3$, $R_4$ and $R_5$, and A and $A_1$, have any of the values defined in the specification.

8 Claims, 3 Drawing Sheets

SMALL MOLECULE INHIBITORS TARGETED AT BCL-2

RELATED APPLICATIONS

This application claims the benefit of the priority date of U.S. Provisional application Ser. No. 60/225,661, filed Aug. 16, 2000. The complete disclosure of this provisional application is incorporated by reference herein.

FIELD OF THE INVENTION

This invention relates to a method for promotion of apoptosis in tumor cells using tricyclo-dibenzo-diazocine-dioxides, non-peptide pharmaceuticals, which are cell permeable small molecules that bind to a pocket of Bcl-2 and block the Bcl-2 anti-apoptotic function in cancer cells and tumor tissue exhibiting Bcl-2 protein overexpression. The compounds, and pharmaceutical compositions comprising these compounds, may be used in the treatment of cancerous disease either alone or in combination with chemotherapeutic or other drugs.

BACKGROUND OF THE INVENTION

Apoptosis, or programmed cell death is important for normal development, host defense and suppression of oncogenesis and faulty regulation of apoptosis has been implicated in cancer and many other human diseases. Bcl-2 was originally identified at the chromosomal breakpoint of t(14;18)-bearing B-cell lymphomas and belongs to a growing family of proteins which regulates apoptosis. (Reed, J. C. Mini-review: Cellular mechanisms of disease series Bcl-2 and the regulation of programmed cell death. *J. Cell. Biol.* 1994, 124, 1–6; Reed, J. C.; Double identity for proteins of the Bcl-2 family. *Nature* 1997, 387, 773–776; Hawkins, C. J.; Vaux, D. L. Analysis of the role of bcl-2 in apoptosis. *Immunological Reviews* 1994, 142, 127–139; Minn, A. J.; Swain, R. E.; Ma, A.; Thompson, C. B. Recent progress on the regulation of apoptosis by bcl-2 family members. *Advances in Immunology* 1998, 70, 245–279). The Bcl-2 family of proteins now includes both anti-apoptotic molecules such as Bcl-2 and Bcl-$X_L$ and pro-apoptotic molecules such as Bax, Bak, Bid and Bad. These molecules play a crucial role in regulating apoptosis (Chao, D. T.; Korsmeyer, S. J. Bcl-2 family: regulators of cell death. *Annu.Rev.Immunol.* 1998, 16, 395–419). As an apoptotic member of this family, Bcl-2 contributes to cancer cell progression by preventing normal cell turnover caused by physiological cell death mechanisms. Overexpression of Bcl-2 has been observed in 70% of breast cancer and many other forms of cancer (Buolaniwini, J. K. Novel anticancer drug discovery. *Curr. Opin. Chem. Biol.* 1999, 3, 500–509). The expression levels of Bcl-2 proteins also correlate with resistance to a wide spectrum of chemotherapeutic drugs and γ-radiation therapy (Reed, J. C.; Miyashita, T.; Takayama, S.; Wang, H.-G.; Sato, T.; Krajewski, S.; Aime-Sempe, C.; Bodrug, S.; Kitada, S.; Hanada, M. Bcl-2 family proteins: Regulators of cell death involved in the pathogenesis of cancer and resistance to therapy. *J. Cell. Biochem.* 1996, 60, 23–32; Reed, J. C. Bcl-2 family proteins: strategies for overcoming chemoresistance in cancer. *Advances in Pharmocology* 1997, 41, 501–553; Strasser, A.; Huang, D. C. S.; Vaux, D. L. The role of the bcl-2/ced-9 gene family in cancer and general implications of defects in cell death control for tumorigenesis and resistance to chemotherapy. *Biochem. Biophys. Acta* 1997,1333, F151–F189; DiPaola, R. S.; Aisner, J. Overcoming bcl-2- and p53-mediated resistance in prostate cancer. *Semin. Oncol.* 1999, 26, 112–116).

Biological approaches targeted at Bcl-2 using anti-sense oligonucleotides or single chain antibodies have been shown to enhance tumor cell chemosensitivity (Ziegler, A.; Luedke, G. H.; Fabbro, D.; Altmann, K. H.; Stahel, R. A.; Zangemeister-Wittke, U. Induction of apoptosis in small-cell lung cancer cells by an antisense oligodeoxynucleotide targeting the Bcl-2 coding sequence. *J. Natl. Cancer. Inst.* 1997, 89, 1027–1036; Webb, A.; Cunningham, D.; Cotter, F.; Clarke, P. A.; Di Stefano, F.; Ross, P.; Corpo, M.; Dziewanowska, Z. Bcl-2 antisense therapy in patients with non-hodgkin lymphoma. *Lancet* 1997, 349, 1137–1141; Cotter, F. E. Phase I clinical and pharmacokinetic study of bcl-2 antisense oligonucleotide therapy in patients with non-hodgkin's lymphoma. *J. Clin. Oncol.* 2000, 18, 1812–1823; Piche, A.; Grim, J.; Rancourt, C.; Gomez-Navarro, J.; Reed, J. C.; Curiel, D. T. Modulation of Bcl-2 protein levels by an intracellular anti-Bcl-2 single-chain antibody increases drug-induced cytotoxicity in the breast cancer cell line MCF-7. *Cancer Res.* 1998, 58, 2134–2140).

It has been shown that an anti-sense oligonucleotide (G3139) (Raynaud, F. I.; Orr, R. M.; Goddard, P. M.; Lacey, H. A.; Lancashire, H.; Judson, I. R.; Beck, T.; Bryan, B.; Cotter, F. E. Pharmacokinetics of G3139, a phosphorothioate oligodeoxynucleotide antisense to bcl-2, after intravenous administration or continuous subcutaneous infusion to mice. *J. Pharmacol. Exp. Ther.* 1997, 281, 420–427), designed to hybridize to sequence in bcl-2 mRNA, inhibits Bcl-2 expression, induces apoptosis and inhibits cell growth in human breast cancer cells having Bcl-2 overexpression (Chen, H. X., Marchall, J. L., Trocky, N., Baidas, S., Rizvi, N., Ling, Y., Bhagava, P., Lippman, M. E., Yang, D., and Hayes, D. F. A Phase I study of bcl-2 antisense G3139 (Genta) and weekly docetaxel in patients with advanced breast cancer and other solid tumors. Proceedings of American Society of Clinical Oncology, 2000). Importantly, synergistic effects and complete tumor regression were observed in vivo in the combined treatments of G3139 with docetaxel. Therefore, Bcl-2 represents a highly attractive target for the development of a novel therapy for the treatment of many forms of cancers.

The experimental 3D structures of BCl-$X_L$ monomer (Muchmore, S. W.; Sattler, M.; Liang, H.; Meadows, R. P.; Harlan, J. E.; Yoon, H. S.; Nettesheim, D.; Chang, B. S.; Thompson, C. B.; Wong, S. -L.; Ng, S. -C.; Fesik, S. W. X-ray and NMR structure of human Bcl-$X_L$, an inhibitor of programmed cell death. *Nature* 1996, 381, 335–341; Aritomi, M.; Kunishima, H.; Inohara, N.; Ishibashi, Y.; Ohta, S.; Morikawa, K. Crystal structure of rat BCl-$X_L$ Implications for the function of the Bcl-2 protein family. *J. Biol. Chem.* 1997, 272, 27886–27892), and Bcl-$X_L$ in complex with Bak BH3 (Michael, S.; Heng, L.; David, N.; Robert, P. M.; John, E. H.; Matthias, E.; Ho Sup, Y.; Suzanne, B. S.; Brian, S. C.; Andy, J. M.; Craig, B. T.; Stephen, W. F. Structure of Bcl-XL-Bak peptide complex: recognition between regulators of apoptosis. *Science* 1997, 275, 983–986), (Bcl-2 homology domain 3), peptide revealed that BH1, BH2 and BH3 domains of Bcl-$X_L$ form a hydrophobic binding pocket into which Bak BH3 domain binds. Since Bcl-2 and Bcl-$X_L$ share a high degree of homology in their amino acid sequences (45% of identity and 56% of similarity), analysis of the 3D structure of Bcl-2 modeled from the NMR and X-ray structures of its highly homologous protein Bcl-XL showed that Bcl-2 has a binding pocket similar to that found in BCl-$X_L$. This binding pocket in Bcl-2 appears to be essential for its anti-apoptotic function since mutations at this site abolished this function (Cosulich, S. C.; Worrall, V.; Hedge, P. J.; Green, S.; Clarke, P. R. Regulation of apoptosis by HH3 domains in a cell-free system. *Curr. Biol* 1997, 7, 913–920; Yin, X.-M.; Oltval, Z. N.; Korsmeyer, S. J. BH1 and BH2 domains of Bcl-2 are required for inhibition of apoptosis and heterodimerization with Bax. *Nature* 1994, 369, 321–323). Furthermore, synthetic, cell permeable peptides binding to this pocket in Bcl-2 induce apoptosis in vitro and have in vivo activity in suppressing human myeloid leukemia growth (Holinger, E. P.; Chittenden, T.; Lutz, R. J. Bak BH3 peptides antagonize Bcl-$X_L$ function and induce apoptosis through cytochrome independent activation of caspases. *J. Biol. Chem.* 1999, 274, 13298–13304; Michael, S.; Heng, L.; David, N.; Robert, P. M.; John, E. H.; Matthias, E.; Ho Sup, Y.; Suzanne, B.S.; Brian, S. C.; Andy, J. M.; Craig, B. T.; Stephen, W. F. Structure of Bcl-XL-Bak peptide complex: recognition between regulators of apoptosis. *Science* 1997, 275, 983–986; Wang, J.-L.; Zhang, Z.-J.; Choksim S.; Shan, S.; Lu, Z.; Croce, C. M.; Alnemri, E. S.; Korugold, R.; Hunag, Z. Cell permeable bcl-2 binding peptides: a chemical approach to apoptosis induction in tumor cells. *Cancer Res.* 2000, 60, 1498–1502). Therefore, non-peptide, drug-like, cell permeable small molecules that bind to this pocket of Bcl-2 block its anti-apoptotic function in cancer cells with Bcl-2 protein overexpression.

The Bcl-2 family of proteins now includes both pro-apoptotic molecules, such as Bax, Bak, Bid and Bad, and anti-apoptotic molecules such as Bcl-2, Bcl-$X_L$, Bcl-W, and Mcl-1. These molecules play a crucial role in regulating apoptosis or programmed cell death (Gross, A.; McDonnell, J. M.; Dorsmeyer, S. J. Bcl-2 family members and the mitochondria in apoptosis. *Genes & Development* 1999, 13, 1899–1911; Hawkins, C. J.; Vaux, D. L. The role of the Bcl-2 family of apoptosis regulatory proteins in the immune system. *Semin. Immunol.* 1997, 9, 25–33; Chao, D. T.; Korsmeyer, S. J. Bcl-2 family: regulators of cell death. *Annu. Rev. Immunol.* 1998, 16, 395–419; Reed, J. C. Bcl-2 family proteins. *Oncogene* 1998, 18, 3225–3236; Park, J. R.; Hockenbery, D. M. Bcl-2, a novel regulator of apoptosis. *J. Cell. Biochem.* 1996, 60, 12–17; Reed, J. C. Mini-review: Cellular mechanisms of disease series Bcl-2 and the regulation of programmed cell death. *J. Cell. Biol.* 1994, 124, 1–6; Reed, J. C.; Double identity for proteins of the Bcl-2 family. *Nature* 1997, 387, 773–776; Reed, J. C.; Miyashita, T.; Takayama, S.; Wang, H.-G.; Sato, T.; Krajewski, S.; Aime-Sempe, C.; Bodrug, S.; Kitada, S.; Hanada, M. Bcl-2 family proteins: Regulators of cell death involved in the pathogenesis of cancer and resistance to therapy. *J. Cell. Biochem.* 1996, 60, 23–32; Adams, J. M.; Cory, S. The Bcl-2 protein family: arbiters of cell survival. *Science* 1998, 281, 1322–1326; Hawkins, C. J.; Vaux, D. L. Analysis of the role of bcl-2 in apoptosis. *Immunological Reviews* 1994, 142, 127–139). As a pro-apoptotic member of this family, Bcl-2 contributes to cancer cell progression by preventing normal cell turnover caused by physiological cell death mechanisms. Biological approaches targeted at Bcl-2 using anti-sense oligonucleotides or single chain antibodies have previously been shown to enhance tumor cell chemosensitivity (Reed, J. C. Bcl-2 family proteins: strategies for overcoming chemoresistance in cancer. *Advances in Pharmocology* 1997, 41, 501–553; Strasser, A.; Huang, D. C. S.; Vaux, D. L. The role of the bcl-2/ced-9 gene family in cancer and general implications of defects in cell death control for tumourigenesis and resistance to chemotherapy. *Biochem. Biophys. Acta* 1997, 1333, F151–F189; DiPaola, R. S.; Aisner, J. Overcoming bcl-2- and p53-mediated resistance in prostate cancer. *Semin. Oncol.* 1999, 26, 112–116; Ziegler, A.; Luedke, G. H.; Fabbro, D.; Altmann, K. H.; Stahel, R. A.; Zangemeister-Wittke, U. Induction of apoptosis in small-cell lung cancer cells by an antisense oligodeoxynucleotide targeting the Bcl-2 coding sequence. *J. Natl. Cancer. Inst.* 1997, 89, 1027–1036; Webb, A.; Cunningham, D.; Cotter, F.; Clarke, P. A.; Di Stefano, F.; Ross, P.; Corpo, M.; Dziewanowska, Z. Bcl-2 antisense therapy in patients with non-hodgkin lymphoma. *Lancet* 1997,349, 1137–1141). It has been shown that an anti-sense oligonucleotide (G3139)designed to hybridize sequence in Bcl-2 MRNA inhibits Bcl-2 expression, induces apoptosis, inhibits cell growth in soft-agar colony formations in human breast cancer cells with Bcl-2 protein overexpression. Importantly, synergistic effects and complete tumor regression were observed in vivo in the combined treatments of G3139 with docetaxel. Thus, inhibition of the anti-apoptotic function of Bcl-2 proteins represents an attractive strategy for a therapeutic method for the treatment of cancer.

Limitations associated with use of large molecules such as proteins and polypeptides as therapeutic agents are the following: poor oral availability, poor in vivo stability and high cost. More desirable therapeutics would therefore be non-peptide, cell permeable, small molecules which effectively bind to this pocket of Bcl-2 which blocks the anti-apoptotic function in cancer and promotes cell death in tumors.

SUMMARY OF THE INVENTION

Figure 1:
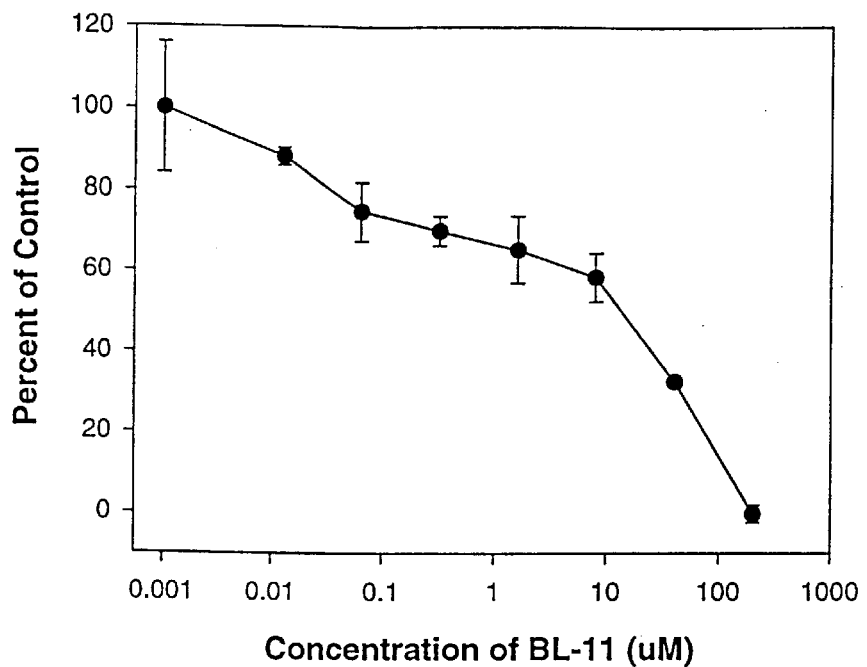
FIG. 1. Illustrates the binding of the compound of formula II to Bcl-2 protein in vitro as measured by a competitive fluorescence polarization assay. The data points represent the mean of three independent experiments. Bcl-2 used in this assay was a GST-fused soluble protein (Santa Cruz Biotechnology, Inc., CA) and Flu-Bak-BH3 peptide (sequence GQVGRQLAIIGDDINR, SEQ ID NO:1) derived from Bak BH3 domain.

The present invention provides a method for promotion of cell death in tumor cells using tricylo-dibenzo-diazocine-dioxides that bind to a pocket of Bcl-2 and block the Bcl-2 anti-apoptotic function. Accordingly, the invention provides a method of use of a compound of the general structural Formula (I):

Formula (I)

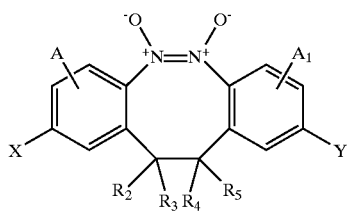

wherein X and Y are each independently hydrogen, OR or $OR_1$;

wherein R and $R_1$ are each independently hydrogen, $(C_1-C_6)$ alkyl, $(C_2-C_6)$ alkenyl, $(C_3-C_8)$ cycloalkyl, phenyl or trifluoromethyl;

wherein $R_2$, $R_3$, $R_4$ and $R_5$ are each independently hydrogen, hydroxy, $(C_1-C_6)$ alkyl, $(C_2-C_6)$ alkenyl, $(C_3-C_8)$ cycloallyl, phenyl, $(C_1-C_6)$ alkoxy, trifluoromethyl, amino, $(C_1-C_6)$ monoalkylamino, or $(C_1-C_6)$ dialkylamino;

A and $A_1$ are each independently 1 to 3 substituents selected from the group consisting of hydrogen, $(C_1-C_6)$ alkyl, $(C_1-C_6)$ alkenyl, fluorine, chlorine, bromine, iodine, $(C_1-C_6)$ alkyl-alkoxy, amino, $(C_1-C_6)$ alkylamino and $(C_1-C_6)$ dialkylamino; and pharmaceutically acceptable salts thereof.

In another embodiment: A and $A_1$=H; $R_2$, $R_3$, $R_4$ and $R_5$=H; and X and Y=$OCH_3$; to yield a compound of Formula II, (2,9-dimethoxy-11,12-dihydrodibenzo[c,g][1,2] diazocine-5,6-dioxide).

Formula II

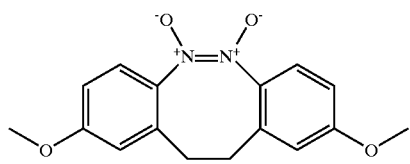

The method of use of pharmaceutically acceptable salts of the above compounds are included within the scope of the present invention, as are uses of formulations of substituted tricyclo-dibenzo-diazocine-dioxides with pharmaceutically acceptable carriers.

The invention also provides pharmaceutical compositions comprising a compound of the invention.

The invention also provides a therapeutic method comprising treating a condition characterized by the pathological proliferation of mammalian cells, such as tumors cells, (e.g. breast cancer and myeloid leukemia, in preferred embodiments), by administering to a mammal or a human afflicted with such a condition an effective amount of a substituted tricyclo-dibenzo-diazocine-dioxide with a pharmaceutically acceptable carrier.

Without being limited by theory, it is believed that compounds of the present invention, which bind to a pocket of Bcl-2, will find use in cancer treatment through the initiation of cancer cell death by apoptosis.

The substituted tricyclo-dibenzo-diazocine-dioxide compounds of the present invention exhibit distinct advantages over the prior art. These compounds have merit for several reasons, including good oral availability, good in vivo stability, and low cost.

DETAILED DESCRIPTION OF THE INVENTION

Specific and preferred values listed below for radicals, substituents, and ranges are for illustration only; they do not exclude other defined values or other values within defined ranges for the radicals and substituents.

The groups $(C_1-C_6)$ alkyl, $(C_2-C_6)$ alkenyl, $(C_1-C_6)$ alkoxy, and $(C_1-C_6)$ dialkylamino, correspond in the formulae I and II to carbon, oxygen and nitro atoms or groups substituted with hydrocarbon substituents which can be either branched or straight chain carbon groups containing the number of carbon atoms designated in parentheses. All terms such as alkoxy, hydroxy, phenyl, fluorine, chlorine, bromine, iodine are terms that would be readily recognized.

It will be appreciated by those skilled in the art that compounds of the invention having one or more chiral center(s) may exist in and be isolated in optically active racemic forms. Some compounds may exhibit polymorphism. It is to be understood that the present invention encompasses any racemic, optically active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine the ability of a compound to promote apoptosis using the tests described herein, or using other tests which are well known in the art.

Biological Testing

The following in vitro binding and cellular assays have been used to determine the activity and specificity of these candidate small molecule inhibitors.

Candidate small molecule inhibitors are identified, for example, by using a modeled 3D structure of Bcl-2 to screen components from the National Career Instutute's 3D-database of 225,000 small molecules using the publically available program DOCK.

Bcl-2 Binding Assay

A sensitive and quantitative in vitro binding assay using an established fluorescence polarization (FP) based method (Wang, J. -L.; Zhang, Z -J.; Choksi, S.; Sjam. S.; Lu, Z.; Croce, C. M.; Alnemri, E. S.; Komgold, R.; Huang, Z. Cell permeable bcl-2 binding peptides: a chemical approach to apoptosis induction in tumor cells. Cancer Res. 2000, 60, 1498–1502). Using this method, a binding affinity of 0.2 $\mu$M (Kd) was obtained between the Bak-BH3 peptide and the Bcl-2, consistent with the value reported in the literature. Using this binding assay, small molecules were screened for their binding activity. Nine Compounds display a binding affinity for Bcl-2 with an IC from 11 $\mu$M to 100 $\mu$M.

Through the binding assay, it is demonstrated that the compound of Formula II inhibits the binding of the Bak-BH3 peptide to Bcl-2 in vitro. (FIG. 1). Because of the importance of this surface pocket to the anti-apoptotic function of Bcl-2, it appears that the binding of the compound of Formula II to Bcl-2 inhibits the antiapoptotic function of Bcl-2 in cells. This inhibition in turn induces apoptosis in cells overexpressing Bcl-2 protein, as shown herein.

Figure 2:
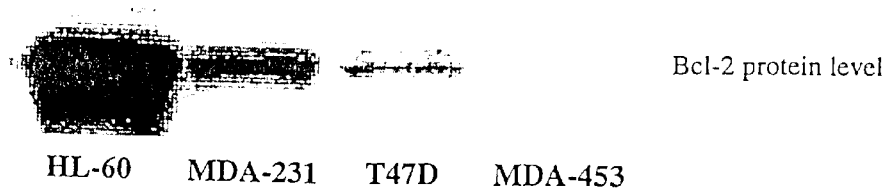
FIG. 2. Illustrates the level of Bcl-2 protein expression in cancer cell lines as detected by Western blotting. 40 µg cell lysates are resolved in 16% SDS polyacryamide gel electrophoresis, detected by the monoclonal anti-BCL2 antibody (Oncogene Research Products, Cambridge, Mass.), and visualized by an ECL™ Western blotting detection system (Amersham Pharmacia Biotech UK Limited, Buckinghamshire, England).

Bcl-2 protein expression in human breast and other cancer cell line is characterized herein. Cell lines MCF-7, MDA-231 and MDA-361 express high levels of Bcl-2; MDA-468, BT474 and MDA-435 express median levels. T47D expresses a very low but detectable, whereas MDA-453 does not express detectable Bcl-2 (FIG. 2). Human myeloid leukemia cell HL-60 expresses the highest level of Bcl-2 protein among all the cell lines examined. Accordingly, MDA-231 and HL-60 cell lines with high Bcl-2 expression are positive cells and MDA-453 and T47D are negative control cells. The level of Bcl-2 protein expression is detected by Western blotting.

Using a Hoechst Dye assay, cells are treated at different doses for 12 hours and apoptotic cells are visually identified and counted under the microscope. Induction of apoptosis is evident after the treatment with Formula II at 10 $\mu$M in MDA-453 or T 47D cell lines, cells with low Bcl-2 expression. At these doses, significant apoptosis in MDA-231 and HL-60 cells is induced.

Figure 3:
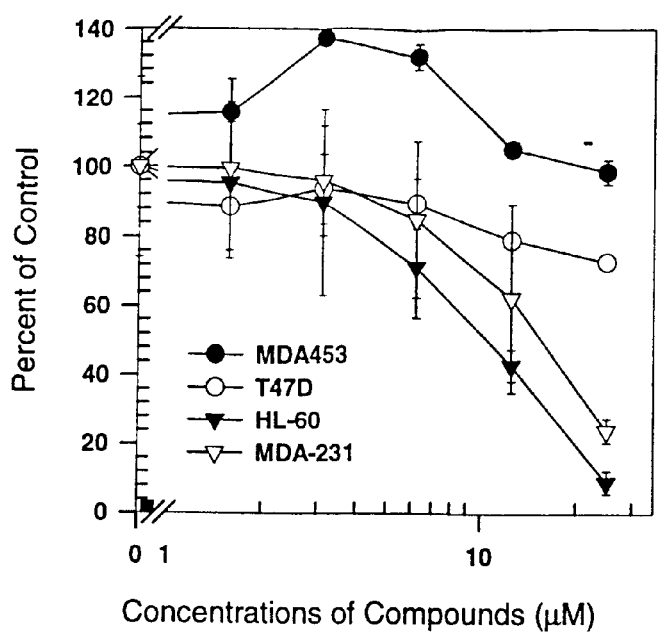
FIG. 3. Illustrated the effects of the compound of formula II on cell viability. Cells are plated in 24-well plates, incubated with said compound at appropriate concentrations for 14 hr. Cell viability is determined by trypan blue exclusion with hemocytometer. Percent of viable cells, as compared with untreated cells, is plotted against drug concentration.

The Annexin-V FACS assay yields a more quantitative assessment of the ability of Formula II to induce of apoptosis in HL-60 and MDA-231 cells. MDA-231 cells treated with 0 (untreated), 4 and 10 $\mu$M of Formula II for 24 hours provide 0, 13% and 20.0% apoptotic cells, respectively, while HL-60 cells treated with 0, 5, 10, and 20 $\mu$M of Formula II for 24 hours provide 0, 24%, 31% and 67% of apoptotic cells, respectively (FIG. 3). Therefore, Formula II induces apoptosis in a highly dose-dependent manner in MDA-231 and HL-60 cell lines with Bcl-2 protein overexpression.

Inhibition of Cell Viability

The ability of Formula II in inhibiting cell viability in cancer cells with Bcl-2 protein overexpression is demonstrated. When HL-60 or MDA-231 cells are exposed to Formula II, the inhibitor shows a dose-dependent cell killing in the trypan-blue exclusion cell survival assay with $IC_{50}$ values of 12 $\mu$M and 15 $\mu$M, respectively. The ability of Formula II to inhibit cell viability is highly specific and correlates well with the Bcl-2 protein expression level in these cancer cells.

In Vivo Antitumor Activity Experiments

The human breast cancer model is established in nude mice. BALB/c female nude mice (nu/nu) are obtained from Taconic Inc. Mice are 4–6 weeks old. All manipulations are performed under sterile condition. Tumor xenografts are established by injecting MDA-MD-231 cells ($1 \times 10^6$ cells) into two side pads. Tumors are measured with a caliper in three dimensions, length, width and high. Tumor volumes are calculated by (length X width X high). Treatments are initiated on day 7 post inoculation; the largest diameter reaches 5–7 mm and volume reaches 40 mm$^3$ at this time.

Bcl-2 small molecule inhibitors are used alone or in combination with other chemotherapy agents such as Docetaxel (Taxotere, TXT), Paclitaxel (taxol, tax), Cisplatin, 5-FU, Doxrubincin, epipodophyllotoxin (VP-16) and cyclophosphamide in mice bearing transplanted MDA-MB-23 tumors for determining the efficacy dosage for this tumors. Sub-optimal dose selected and used in combination studies are Docetaxel at 7.5 mg /kg or 3.75 mg/kg intravenously (i.v.) once a week; Paclitaxel (taxol, tax) at 7.5 mg/kg, three times per week intraperitoneally (i.p.); Cisplatin at 10 mg/kg, ip. once a week; 5-FU 10 mg /kg, three times per week i.p.; Doxrubincin 4 mg/kg, twice a week i.p.; epipodophyllotoxin (VP-16) 80 mg/kg, once a week i.p.; cyclophosphamide at 100 mg/kg, once a week i.p. The combination treatments are performed for 3 weeks.

The doses of the Bcl-2 inhibitors small molecule inhibitors of the present invention preferably range from 1 mg/kg to 100 mg/kg, daily or twice a week, administered in 0.1 ml i.p. for 3 weeks. Approximate tumor sizes and body weight are measured twice a week. Average volumes and standard deviations are calculated for each group and plotted.

For treating large tumors, the tumors are established as described above. Treatment is started on days 12, and on day 21, and the tumor's largest diameter reached 6–10 mm and 10–15 mm, and tumors volume reached volume of 93.2 and 559 mm$^3$, respectively.

For histological and Western analysis, the animals are sacrificed after treatment with the appropriate ODN's at the indicated concentration, and tumor are removed at various times from day 2 to day 18 following treatment for the purpose of detecting bcl-2 level and for histologic examination. 12 time points are preferably selected at 40 hrs, 48 hrs, day 3, 4, 6, 9, 10, 11, 14, 16, 17 and day 18. Tumor tissue samples collected from mice are fixed in 10% Formalin solution, and then embedded in paraffin blocks, from which 4 $\mu$m sections are cut and stained with Hematoxylin and Eosin (HE).

Statistical Analysis

The antitumor activity curves for the Bcl-2 small molecule inhibitors are plotted with the observation time on the X-axis, and corresponding tumor volume (geometric mean) on the Y-axis. The area under the curve (AUC) was calculated by Tai's mathematical model for each curve, and is shown as geometric means and 95% Ontidencial interrals. The difference of AUC among treatment groups is compared by ANOVA.

PREFERRED COMPOUNDS

The chemical synthesis of compounds of the present invention is well within the ability of those of ordinary skill in the art, particularly a known compound such as Formula II. The chemical modifications of these compounds can be carried out using standard synthetic methods.

In cases where compounds of Formula I and Formula II are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of Formula I and Formula II can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its slats can be prepared in water, and/or optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pureform, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

All publications, patents, and patent documents referred to herein are hereby incorporated in their respective entireties by reference.

The invention has been described with reference to the foregoing specific and preferred embodiments and methods. However, it should be understood that amny variations may be made while remaining within the spirit and scope of the invention. Therefore, the foregoing examples are not limiting, and the scope of the invention is intended to be limited only by the following claims.

What is claimed is:

1. A method for promoting apoptosis in cells overexpressing Bcl-2 in a subject comprising administering to said subject a therapeutically effective amount of a compound of the general formila:

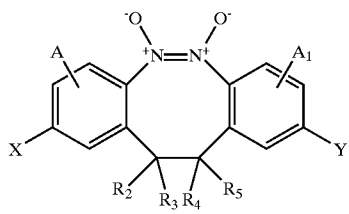

wherein X and Y are each independently hydrogen, OR or OR1; wherein R and R1 are each independently hydrogen, (C1–C6) alkyl, (C2–C6) alkenyl, (C3–C8) cycloalkyl, phenyl or trifluoromethyl; wherein R2, R3, R4 and R5 are each independently hydrogen, hydroxy, (C1–C6) alkyl, (C2–C6) alkenyl, (C3–C8) cycloalkyl, phenyl, (C1–C6) alkoxy, trifluoromethyl, amino, (C1–C6) monoalkylamino, or (C1–C6) dialkylainino; A and Al are each independently 1 to 3 substituents selected from the group consisting of hydrogen, (C1–C6) alkyl, (C1–C6) alkenyl, fluorine, chlorine, bromine, iodine, (C1–C6) alkyl-alkoxy, amino, (C1–C6) alkylarnino and (C1–C6) dialkylamino; and pharmaceutically acceptable salts thereof.

2. The method of claim 1, wherein the compound is administered to a mammal.

3. The method of claim 2, wherein the mammal is a human.

4. The method of claim 1, wherein the compound is

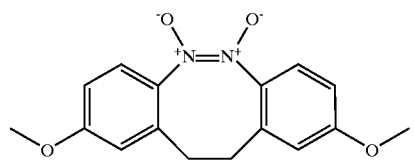

(2,9-dimetboxy-11,12-dihydrodibenzo-[c,g][1,2]diazocine-5,6-dioxide), and pharmaceutically acceptable salts thereof.

5. The method of claim 4 wherein the compound is administered to a mammal.

6. The method of claim 5 wherein the mammal is a human.

7. A pharmaceutical composition comprising a compound of the general formula:

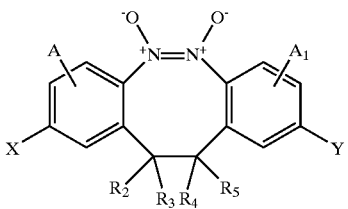

wherein X and Y are each independently hydrogen; OR or OR1; wherein R and R1 are each independently hydrogen, (C1–C6) alkyl, (C2–C6) alkenyl, (C3–C8) cycloalkyl, phenyl or trifluoromethyl; wherein R2, R3, R4 and R5 are each independently hydrogen, hydroxy, (C1–C6) alkyl, (C2–C6) alkenyl, (C4–C8) cycloalkyl, phenyl, (C1–C6) alkoxy, trifluoromethyl, amino, (C1–C6) monoalkylamino, or (C1–C6) dialkylamino; A and Al are each independently 1 to 3 substituents selected from the group consisting of hydrogen, (C1–C6) alkyl, (C1–C6) alkenyl, fluorine, chlorine, bromine, iodine, (C1–C6) alkyl-alkoxy, amino, (C1–C6) alkylamino and (C1–C6) dialkylaznino; and a pharmaceutically acceptable carrier.

8. A pharmaceutical composition comprising a compound of the general formula:

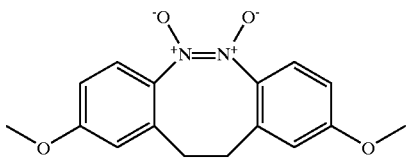

and a pharmaceutically acceptable carrier.

* * * * *